US012569583B2

(12) United States Patent
Nakao

(10) Patent No.: US 12,569,583 B2
(45) Date of Patent: Mar. 10, 2026

(54) ARRANGEMENT STRUCTURE FOR PUMP-TYPE BOTTLE IN AIRCRAFT CABIN

(71) Applicant: The Yokohama Rubber Co., LTD., Tokyo (JP)

(72) Inventor: Kazushi Nakao, Kanagawa (JP)

(73) Assignee: The Yokohama Rubber Co., LTD., Tokyo (JP)

( * ) Notice: Subject to any disclaimer, the term of this patent is extended or adjusted under 35 U.S.C. 154(b) by 211 days.

(21) Appl. No.: 18/249,333

(22) PCT Filed: Apr. 30, 2021

(86) PCT No.: PCT/JP2021/017194
§ 371 (c)(1),
(2) Date: Apr. 17, 2023

(87) PCT Pub. No.: WO2022/085224
PCT Pub. Date: Apr. 28, 2022

(65) Prior Publication Data
US 2023/0390429 A1 Dec. 7, 2023

(30) Foreign Application Priority Data
Oct. 22, 2020 (JP) ................................ 2020-177522

(51) Int. Cl.
*A61L 2/26* (2006.01)
*A61L 2/00* (2006.01)
*B64D 11/00* (2006.01)
(52) U.S. Cl.
CPC .............. *A61L 2/0088* (2013.01); *A61L 2/26* (2013.01); *B64D 11/00* (2013.01); *A61L 2202/15* (2013.01)

(58) Field of Classification Search
CPC ....................................................... A61L 2/26
See application file for complete search history.

(56) References Cited

U.S. PATENT DOCUMENTS

| 1,174,688 | A | * | 3/1916 | Colbert | .................. | A47G 29/24 |
| | | | | | | 248/311.2 |
| 1,929,562 | A | * | 10/1933 | Pierce | ..................... | B60R 11/00 |
| | | | | | | 248/312.1 |
| 2,081,292 | A | * | 5/1937 | Crossley | ................ | A47G 29/18 |
| | | | | | | 248/311.2 |
| 2,883,139 | A | * | 4/1959 | Dobkin | ................... | A47J 47/16 |
| | | | | | | 248/311.2 |
| 4,615,476 | A | * | 10/1986 | Hobbs | .................. | A47K 5/1211 |
| | | | | | | 222/153.09 |

(Continued)

FOREIGN PATENT DOCUMENTS

| EP | 2487110 A2 * | 8/2012 | ............. | B64D 11/02 |
| EP | 2492195 A1 * | 8/2012 | ......... | G01N 21/6456 |

(Continued)

OTHER PUBLICATIONS

Delta, "Five ways Delta is keeping lavatories safe and clean for you", Delta News Hub, [online], Aug. 27, 2020, Internet: <URL: http s://news.delta.com/five-ways- delta-keeping-lavatories-safe-and-clean-you-0>, retrieval date Jul. 9, 2021 J, entire text, all drawings.

(Continued)

*Primary Examiner* — Christopher P Ellis
(74) *Attorney, Agent, or Firm* — Thorpe North & Western

(57) ABSTRACT
A pump-type bottle configured to discharge a disinfectant for hands and fingers is disposed at a wall portion in the aircraft cabin via an arrangement instrument at a height at which a passenger can push down a head portion thereof.

10 Claims, 16 Drawing Sheets

(56) References Cited

U.S. PATENT DOCUMENTS

| | | | |
|---|---|---|---|
| 6,041,974 | A * | 3/2000 | Poitras ..................... A47K 5/12 |
| | | | 222/173 |
| 7,100,872 | B2 | 9/2006 | Quan |
| 7,188,629 | B2 * | 3/2007 | Mehes ..................... A47K 1/09 |
| | | | 206/209.1 |
| 8,668,178 | B2 * | 3/2014 | Ziaylek ................. F17C 13/084 |
| | | | 224/570 |
| 10,342,391 | B2 * | 7/2019 | Beckerman ......... B05B 11/0054 |
| D955,779 | S * | 6/2022 | Carvalho de Oliveira .... D6/545 |
| 11,401,703 | B1 * | 8/2022 | Tsai .......................... E03C 1/04 |
| D1,071,602 | S * | 4/2025 | Schmidt ......................... D6/545 |
| 2016/0288151 | A1 | 10/2016 | Schultz et al. |
| 2018/0170605 | A1 * | 6/2018 | Schriner ............. B65D 1/0261 |
| 2018/0340317 | A1 * | 11/2018 | Voetter .................. E03C 1/021 |

FOREIGN PATENT DOCUMENTS

| | | | | |
|---|---|---|---|---|
| EP | 3277142 | B1 * | 10/2020 | ............. F16M 13/02 |
| EP | 3777624 | A1 * | 2/2021 | ......... B05B 11/1052 |
| EP | 3919384 | A1 * | 12/2021 | ........... A47K 5/1217 |
| EP | 4 234 403 | A1 | 8/2023 | |
| EP | 3777624 | B1 * | 7/2024 | ............. B64D 11/02 |
| JP | 2011-136699 | A | 7/2011 | |
| JP | 2014-534833 | A | 12/2014 | |
| JP | 2016-169004 | A | 9/2016 | |
| JP | 6129129 | B2 * | 5/2017 | |
| JP | 2020-176031 | A | 10/2020 | |
| WO | 2015/162827 | A1 | 10/2015 | |
| WO | WO 2018/102381 | A1 | 6/2018 | |

OTHER PUBLICATIONS

ESSE online, [online], Aug. 5, 2020, Internet: <URL: https://esse-online.jp/interior/243372>, [retrieval date: Jul. 9, 2021], entire text, all drawings, non-official translation (Okuno, Atsuko, "Masks and sterilization gel fit in nicely. There is no reason not to use a 100yen umbrella stand").

* cited by examiner

ARRANGEMENT STRUCTURE FOR PUMP-TYPE BOTTLE IN AIRCRAFT CABIN

TECHNICAL FIELD

The present technology relates to an arrangement structure for a pump-type bottle in an aircraft cabin.

BACKGROUND ART

In recent years, measures for preventing infections with a novel coronavirus have been widely taken in various countries around the world. Most of the infections with the novel coronavirus are said to be caused by touching eyes, a nose, or a mouth with hands and fingers with viruses attached due to contact with objects.

It is preferable to take measures to prevent the infections with the novel coronavirus also in an aircraft cabin.

The present inventor has focused on a pump-type bottle and thought that if a pump-type bottle containing a disinfectant for disinfecting hands and fingers is disposed in an aircraft cabin, passengers and cabin attendants can disinfect their hands and fingers, which is advantageous in preventing the infections with the novel coronavirus in the cabin.

On the other hand, the disinfectant is discharged by pushing down a head portion of the pump-type bottle, and the pump-type bottle needs to be placed at a height at which the head portion can be pushed down.

For this purpose, it is conceivable that a placement platform dedicated to the pump-type bottle is disposed at a predetermined height on a floor of the aircraft cabin.

Unfortunately, disposing such a placement platform needs to have a space for disposing the placement platform on a narrow floor in the cabin.

In addition, the placement platform has a predetermined height, and thus the volume of members constituting the placement platform increases, thus increasing the weight of the structure for disposing the pump-type bottle in the cabin.

SUMMARY

The present technology provides an arrangement structure for a pump-type bottle in an aircraft cabin, which needs no placement platform, needs no space on a floor, enables the pump-type bottle to be disposed in the aircraft cabin while reducing weight, and is advantageous in preventing infections with novel coronavirus in the aircraft cabin.

One embodiment of the present technology is an arrangement structure for a pump-type bottle in an aircraft cabin in which the pump-type bottle that can discharge a disinfectant for hands and fingers is disposed in the aircraft cabin. An arrangement instrument configured to attach the pump-type bottle is provided on a wall portion of the aircraft cabin. The pump-type bottle is disposed at the wall portion by using the arrangement instrument at a height at which a passenger can push down a head portion of the pump-type bottle.

According to the present technology, the pump-type bottle that can discharge a disinfectant for hands and fingers is disposed at a height at which a passenger can push down the head portion by using the arrangement instrument on the wall portion of the aircraft cabin.

Thus, a placement platform dedicated to the pump-type bottle is unnecessary, and the pump-type bottle can be disposed in the cabin without a space on a floor in the cabin.

In addition, since the arrangement instrument that is smaller and lighter than the placement platform is used, it is advantageous in reducing the weight of the structure for disposing the pump-type bottle in the cabin, and the pump-type bottle can be disposed in the cabin while reducing weight.

Therefore, the pump-type bottle that can discharge a disinfectant for hands and fingers can be disposed in the aircraft cabin, which is advantageous in preventing the infections with the novel coronavirus in the aircraft cabin.

DETAILED DESCRIPTION

Next, an aircraft lavatory unit according to an embodiment of the present technology will be described with reference to drawings.

Figure 16:
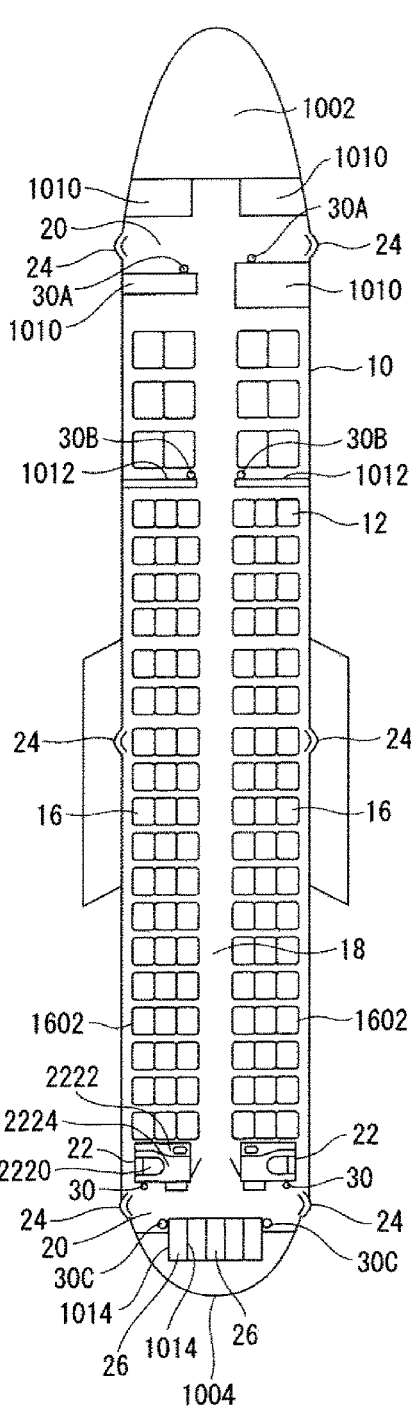
FIG. 16 is a plan view of an aircraft cabin.

Starting from a first embodiment, as illustrated in FIG. 16, a cockpit 1002 is provided in a front portion of a fuselage 10 of an aircraft, a plurality of dividing walls 1010 is provided behind the cockpit 1002, a cabin 12 is provided behind the dividing walls 1010, and a pressure bulkhead 1004 is provided in a rear portion of the fuselage 10.

The cabin 12 includes seat groups 16, a longitudinal aisle 18, a latitudinal aisle 20, and aircraft lavatory units 22.

The longitudinal aisle 18 extends in a front-rear direction of the fuselage 10 between the front portion and the rear portion of the fuselage 10.

Two of the seat groups 16 are provided on the left and right sides of the longitudinal aisle 18.

The seat groups 16 each include a plurality of seat rows 1602 arranged in rows in the front-rear direction of the fuselage 10. The seat rows 1602 each include a plurality of seats facing the front of the fuselage 10 and arrayed in a width direction of the fuselage 10.

The seat groups 16 in the front of the fuselage 10 are first class, the seat groups 16 behind the first class are economy class, and partition walls 1012 are provided between the first class and the economy class.

A plurality of the latitudinal aisles 20 is provided at intervals in the front-rear direction of the fuselage 10, and the latitudinal aisles 20 extend in the width direction of the fuselage 10 and are provided orthogonal to the longitudinal aisle 18.

Boarding entrances 24 are provided at both ends in the extension direction of each of the latitudinal aisles 20.

In the rear portion of the fuselage 10, the aircraft lavatory units 22 are provided on both sides of the longitudinal aisle 18 in front of the latitudinal aisles 20. The aircraft lavatory units 22 are disposed facing both the longitudinal aisle 18 and the latitudinal aisle 20.

A plurality of galleys 26 partitioned by partition walls 1014 is provided behind the latitudinal aisle 20.

The aircraft lavatory unit 22 is disposed behind the seat row 1602 located at the rearmost end of each of the seat groups 16 on a floor of the fuselage 10.

The aircraft lavatory units 22 are configured in a bilaterally symmetrical shape with respect to the longitudinal aisle 18, and the aircraft lavatory unit 22 disposed on the left side of the longitudinal aisle 18 in FIG. 16 will be described.

Figure 1:
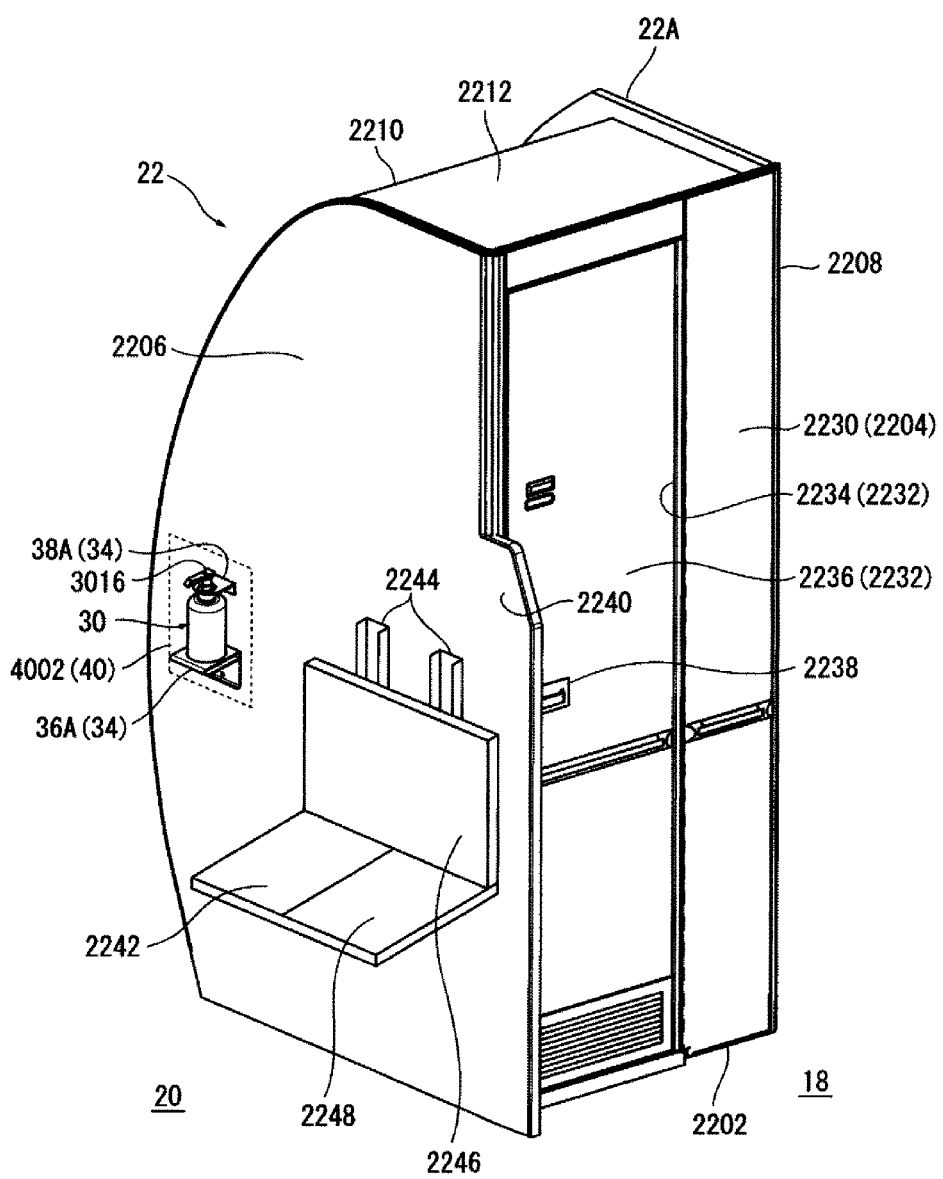
FIG. 1 is a perspective view of an aircraft lavatory unit to which a first embodiment is applied.

As illustrated in FIG. 1, a structural frame 22A of the aircraft lavatory unit 22 includes a bottom wall 2202 placed on the floor, a front wall 2204 facing the longitudinal aisle 18, a first side wall 2206 facing the latitudinal aisle 20, a second side wall 2208 facing the rear of the seat row 1602 located at a rear end, a rear wall 2210 adjacent to a wall portion of the fuselage 10, and a ceiling wall 2212.

As illustrated in FIG. 16, the inside of the structural frame 22A is a lavatory 2224 with a toilet 2220, a sink 2222, and the like.

As illustrated in FIG. 1, the front wall 2204 includes a front wall body 2230 and an entrance 2232 of the aircraft lavatory unit 22 (lavatory 2224) provided lateral to the front wall body 2230.

The entrance 2232 includes an opening 2234 provided lateral to the front wall body 2230 and a door 2236 for opening and closing the opening 2234, and the door 2236 is provided with a handle 2238 for opening and closing operation.

An edge portion of the first side wall 2206 on the boarding entrance 24 side is provided in a curved shape corresponding to the rear wall 2210, a protruding wall 2240 is provided at the first side wall 2206 on the longitudinal aisle 18 side, and an attendant seat 2242 for seating a cabin attendant is provided on the first side wall 2206 by using the protruding wall 2240.

The attendant seat 2242 is for two persons and includes frames 2244 attached to the first side wall 2206, a backrest 2246 attached to the frames 2244, and a seat portion 2248 foldably attached to the frames 2244.

A pump-type bottle 30 that can discharge a disinfectant for hands and fingers is provided at a wall portion in the cabin at a height at which a passenger can push down a head portion 3016 of the pump-type bottle 30.

Here, examples of the wall portion in the cabin includes the plurality of dividing walls 1010 provided behind the cockpit 1002, the partition walls 1012 that separate the first class from the economy class, the partition walls 1014 that partition the plurality of galleys 26, and wall portions constituting the structural frames 22A of the aircraft lavatory units 22.

In the present embodiment, the pump-type bottle 30 is provided at a wall portion constituting the structural frame 22A of each of the two aircraft lavatory units 22 at a height at which a passenger can push down the head portion 3016 of the pump-type bottle 30.

In the following second to seventh embodiments as well as the first embodiment, cases in which the pump-type bottle 30 is provided at a wall portion constituting the structural frame 22A of the aircraft lavatory unit 22 will be described, and the present technology is widely applied to other wall portions in the cabin.

In the first embodiment, the pump-type bottle 30 that can discharge a disinfectant is provided at the first side wall 2206 facing the latitudinal aisle 20 and not having the entrance 2232, and the pump-type bottle 30 is provided at a height at which a passenger can push down the head portion 3016 thereof.

Here, the height of the head portion 3016 at which a passenger can push down the head portion corresponds to, for example, a position about 80 cm to 140 cm above the floor.

The pump-type bottle 30 is provided at a location of the first side wall 2206 near the boarding entrance 24.

In the present embodiment, the pump-type bottle 30 is provided at a location of the first side wall 2206 closer to the boarding entrance 24 than the attendant seat 2242.

Thus, every time passengers use the aircraft lavatory unit 22, they can push down the head portion 3016 of the pump-type bottle 30 to discharge a disinfectant to their hands and fingers and easily disinfect them, which is advantageous in preventing the infections with the novel coronavirus in the aircraft cabin.

Further, since the pump-type bottle 30 that can discharge a disinfectant for hands and fingers is disposed at the first side wall 2206 constituting the latitudinal aisle 20 near the boarding entrance 24, passengers can disinfect their hands and fingers when boarding the aircraft and then board the aircraft, which is advantageous in preventing the infections with the novel coronavirus in the cabin.

Furthermore, since the pump-type bottle 30 that can discharge a disinfectant for hands and fingers is disposed lateral to the attendant seat 2242, cabin attendants can easily disinfect their hands and fingers by using the pump-type bottle 30 when sitting on or leaving the attendant seat 2242, which is advantageous in preventing passengers from being infected with the novel coronavirus via the cabin attendants in the cabin.

Figure 2:
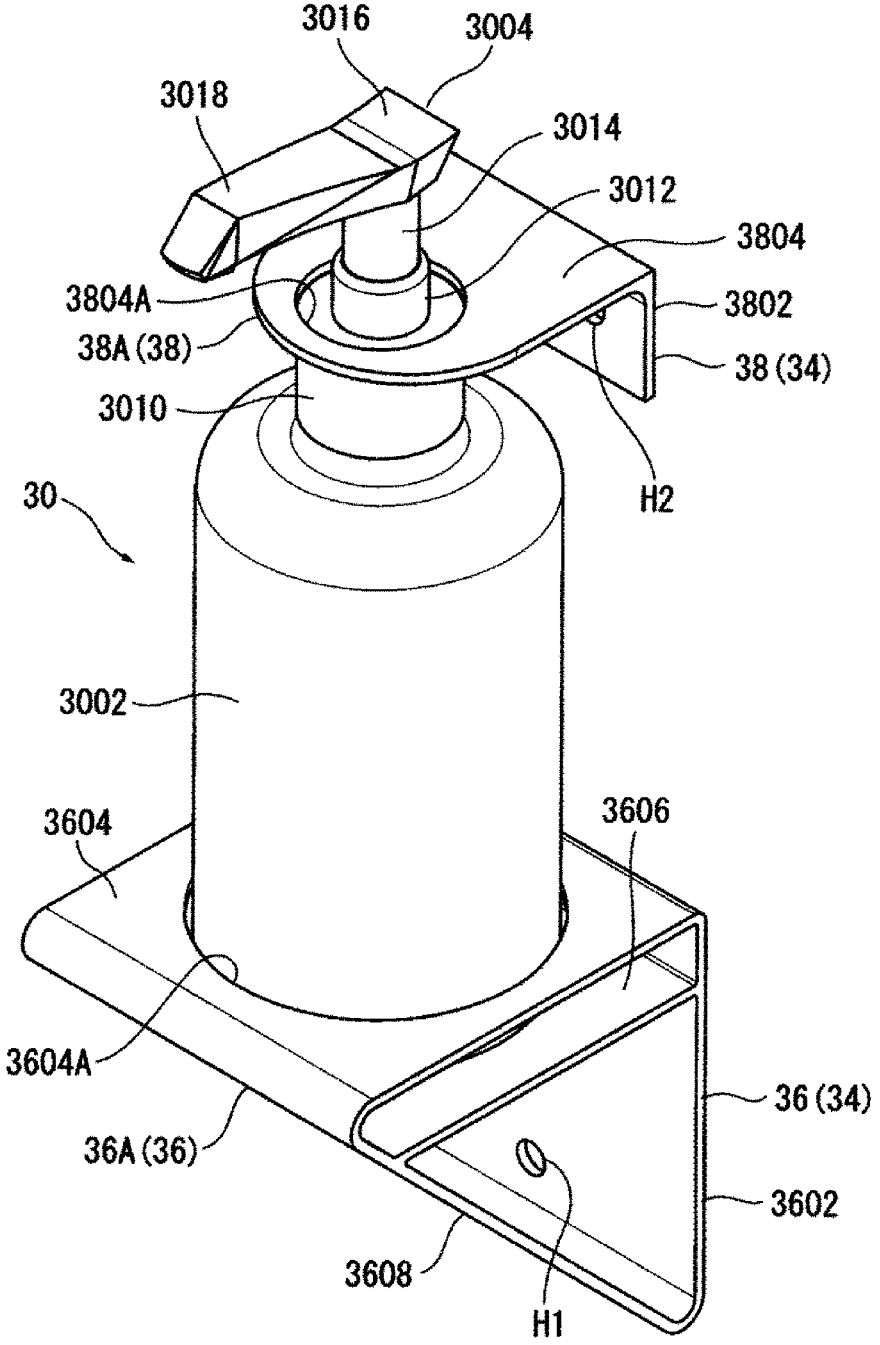
FIG. 2 is a perspective view illustrating a pump-type bottle disposed at a first side wall by using an arrangement instrument according to the first embodiment, in which male thread members are omitted to clarify the structure of the arrangement instrument.

As illustrated in FIG. 2, the pump-type bottle 30 includes a container 3002 containing a disinfectant for hands and fingers, and a pump dispenser 3004 for discharging the disinfectant in the container 3002. The disinfectant for hands and fingers may be any disinfectant that is discharged from a nozzle portion 3018 to hands and fingers and widely includes a liquid or gel disinfectant.

The container 3002 is formed of a cylindrical shape having a uniform outer diameter and includes, at the center of an upper surface, a small diameter portion having a cylindrical shape and protruding upward. The small diameter portion includes a male thread formed on an outer circumferential surface thereof.

The pump dispenser 3004 includes: a hollow cap 3010 to be screwed to the small diameter portion; a cylinder 3012 held by the cap 3010, protruding above the cap 3010, and extending inside the container 3002; a tube attached to a bottom wall of the cylinder 3012 with a first one-way valve interposed, extending downward, and having a lower end located near a bottom surface of the container 3002; a piston that slides in the cylinder 3012 and forms a cylinder chamber between the piston and the bottom wall of the cylinder 3012; a piston rod 3014 protruding above an upper end of the cylinder 3012 from the piston; a spring constantly biasing the piston upward; the head portion 3016 provided at an upper end of the piston rod 3014; the nozzle portion 3018 protruding from the head portion 3016; a disinfectant passage communicating from the piston to the nozzle portion 3018; and a second one-way valve interposed in the disinfectant passage.

Thus, for example, when a hand is released from the head portion 3016 that has been pushed down, the piston is raised by biasing force of the spring to an upper limit position. The rise of the piston causes the pressure in the cylinder chamber to be negative, the second one-way valve is closed, the first one-way valve is opened, and the disinfectant in the container 3002 is sucked into the cylinder chamber via the tube.

When the head portion 3016 is pushed down, the cylinder chamber is compressed by the piston, the second one-way valve is opened, the first one-way valve is closed, the disinfectant in the cylinder chamber rises through the disinfectant passage, and the disinfectant is discharged from the nozzle portion 3018.

As such a pump-type bottle 30, commercially available products having known various structures can be used.

Figure 3:
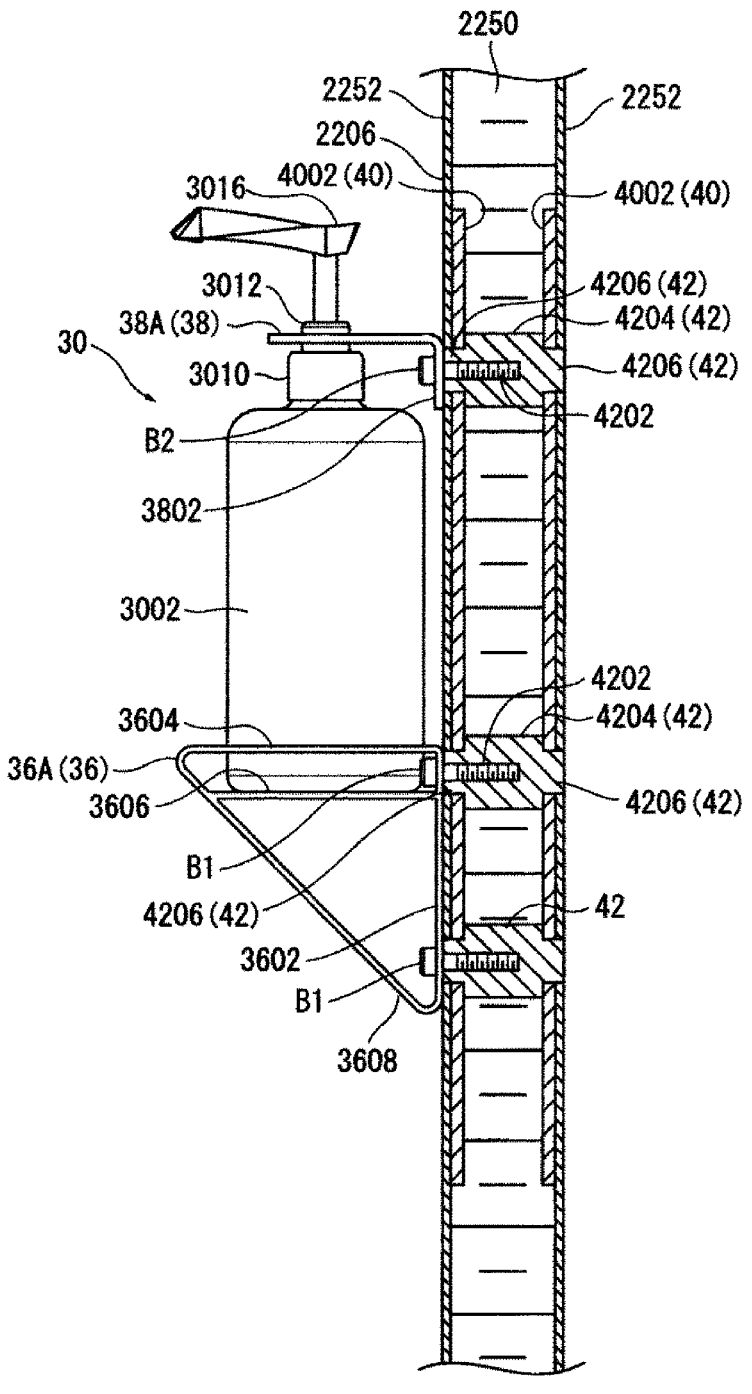
FIG. 3 is a cross-sectional view illustrating the pump-type bottle disposed at the first side wall by using the arrangement instrument according to the first embodiment.

As illustrated in FIGS. 2 and 3, the pump-type bottle 30 is disposed at the first side wall 2206 via an arrangement instrument 34.

The arrangement instrument 34 includes a lower support member 36 that is attached to the first side wall 2206 and supports a lower portion of the pump-type bottle 30 and an upper support member 38 that is attached to the first side wall 2206, separated from the lower support member 36, and supports an upper portion of the pump-type bottle 30.

Specifically, the arrangement instrument 34 includes the lower support member 36 that supports the lower portion of the pump-type bottle 30 while regulating the horizontal movement of the container 3002 and the upper support member 38 that is separated from the lower support member 36 and regulates the upward movement of the pump-type bottle 30 at the upper portion of the pump-type bottle 30.

Figure 4A:
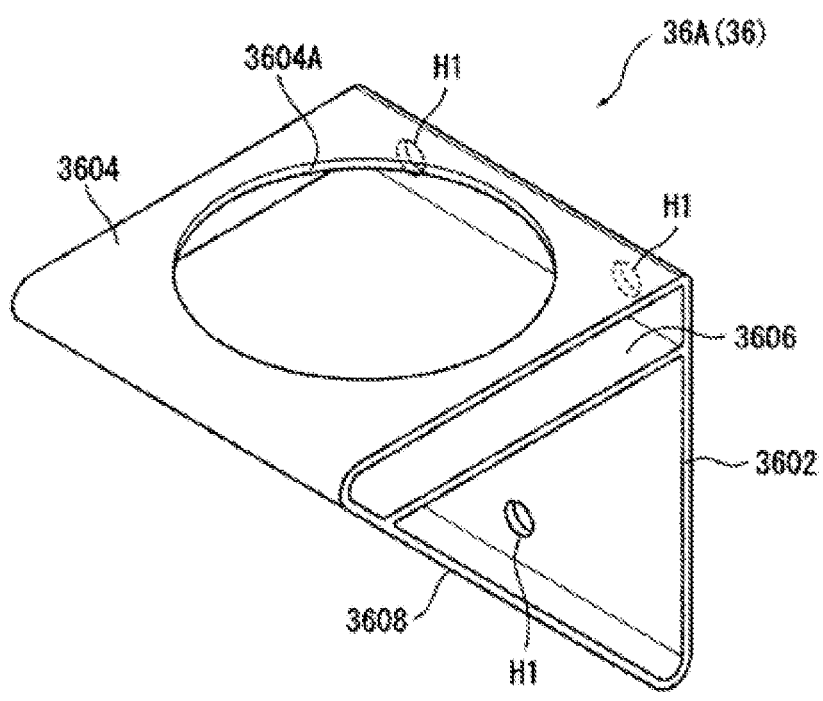
FIG. 4A is a perspective view of a lower bracket according to the first embodiment.
Figure 4B:
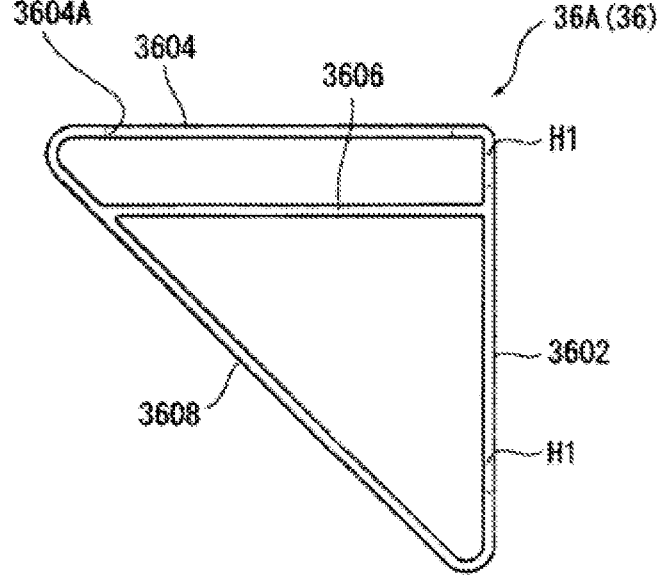
FIG. 4B is a side view thereof.

As illustrated in FIGS. 4A-4B, the lower support member 36 includes a lower bracket 36A to be attached to the first side wall 2206.

The lower bracket 36A is made of an alloy or a fiber reinforced plastic and is preferably made of an aluminum alloy in view of strength, rigidity, lightness, processability, and design. In the present embodiment, the lower bracket 36A is made of an aluminum alloy.

The lower bracket 36A includes a base plate portion 3602, an upper plate portion 3604, a placement plate portion 3606, and a connecting plate portion 3608.

The base plate portion 3602 has a rectangular shape and includes first bolt insertion holes H1 at two locations, both sides of an upper portion of the base plate portion 3602 and at one location, the center of a lower portion of the base plate portion 3602.

As illustrated in FIG. 3, the base plate portion 3602 is placed on the first side wall 2206 and is attached to the first side wall 2206 via first bolts B1 which are male thread members inserted into the first bolt insertion holes H1. In the present embodiment, hexagonal socket bolts to be turned by a hexagonal wrench are used as the first bolts B1.

As illustrated in FIGS. 4A-4B, the upper plate portion 3604 protrudes from the upper end of the base plate portion 3602.

The upper plate portion 3604 includes a lower insertion hole 3604A having a circular shape through which a lower portion of the container 3002 of the pump-type bottle 30 is removably inserted and which regulates the horizontal movement of the lower portion of the container 3002 with the lower portion of the container 3002 inserted.

The placement plate portion 3606 is protruded from a portion of the base plate portion 3602 located below the upper plate portion 3604. A bottom portion of the container 3002 inserted through the lower insertion hole 3604A is placed on the placement plate portion 3606. The placement plate portion 3606 supports the weight of the pump-type bottle 30 receives the load of the pump-type bottle 30 applied when a passenger or a cabin attendant pushes down the head portion 3016.

The connecting plate portion 3608 is disposed protruding obliquely upward from a lower end of the base plate portion 3602 and connects ends of the upper plate portion 3604 and the placement plate portion 3606.

With the base plate portion 3602 attached to the first side wall 2206, all of the base plate portion 3602, the upper plate portion 3604, and the connecting plate portion 3608 extend in the horizontal direction.

In addition to the material having strength and rigidity for constituting the lower bracket 36A, the lower bracket 36A consisting of the base plate portion 3602, the upper plate portion 3604, and the connecting plate portion 3608 has a substantially triangular frame shape in a side view as illustrated in FIG. 4B, in other words, has a closed cross-sectional shape, the shape itself has strength and rigidity, and the lower bracket 36A is provided with strength and rigidity so as to be unbreakable with force of 136 kg-force (kgf) in the vertical direction or force of 136 kg-force (kgf) in the horizontal direction.

Figure 5A:
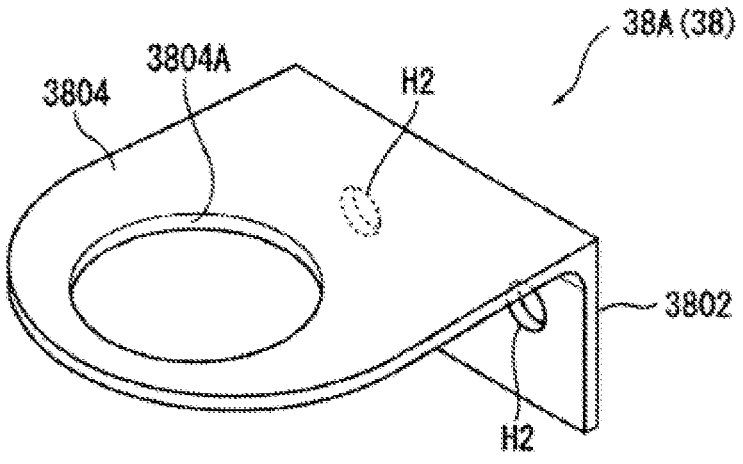
FIG. 5A is a perspective view of an upper bracket according to the first embodiment.
Figure 5B:
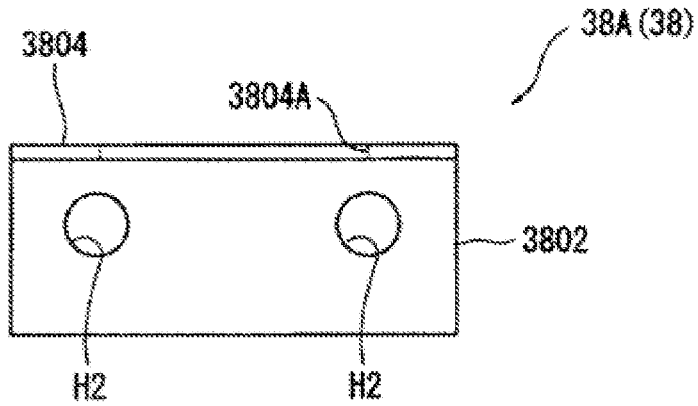
FIG. 5B is a front view thereof.

As illustrated in FIGS. 5A-5B, the upper support member 38 includes an upper bracket 38A to be attached to the first side wall 2206.

Similar to the lower bracket 36A, the upper bracket 38A is made of an alloy or a fiber reinforced plastic and is preferably made of an aluminum alloy in view of strength, rigidity, lightness, processability, and design. In the present embodiment, the upper bracket 38A is made of an aluminum alloy.

Since the upper bracket 38A is a member that regulates the upward movement of the pump-type bottle 30 as will be described later, the upper bracket 38A has a simpler configuration, a smaller size, and a lighter weight than the lower support member 36 and is advantageous in reducing the weight and cost of the upper support member 38, that is, reducing the weight and cost of the arrangement instrument 34.

The upper bracket 38A includes a mounting plate portion 3802 and a protruding plate portion 3804.

The mounting plate portion 3802 has an elongated rectangular shape and includes two second bolt insertion holes H2 in the mounting plate portion 3802.

As illustrated in FIG. 3, the mounting plate portion 3802 is placed on a location of the first side wall 2206 separated upward from the lower bracket 36A and is attached to the first side wall 2206 with second bolts B2 which are male thread members inserted into the second bolt insertion holes H2. In the present embodiment, hexagonal socket bolts to be turned by a hexagonal wrench are used as the second bolts B2.

As illustrated in FIGS. 5A-5B, the protruding plate portion 3804 is disposed protruding from an upper end of the mounting plate portion 3802.

The protruding plate portion 3804 includes an upper insertion hole 3804A through which the upper portion of the pump-type bottle 30 is removably inserted and which regulates the upward movement of the pump-type bottle 30.

In the present embodiment, as illustrated in FIG. 2, the upper insertion hole 3804A is formed to have an inside diameter larger than the outer diameter of the cylinder 3012 constituting the upper portion of the pump-type bottle 30 and smaller than the outer diameter of the cap 3010. Thus, the cap 3010 comes in contact with a portion of the protruding plate portion 3804 around the upper insertion hole 3804A, thus regulating the upward movement of the pump-type bottle 30.

As illustrated in FIG. 3, the wall portions of the structural frame 22A including the first side wall 2206 includes a core 2250 that has a honeycomb structure and is made of a synthetic fibrous material and a surface plate 2252 that is made of a fiber reinforced plastic and attached to both surfaces of the core 2250.

Since it is necessary to reduce the weights of wall portions provided in the aircraft cabin, every wall portion including the bottom wall 2202, the front wall 2204, the first side wall 2206, the second side wall 2208, the rear wall 2210 and the ceiling wall 2212 constituting the structural frame 22A of the aircraft lavatory unit 22 and the other walls provided in the aircraft cabin, for example, the plurality of dividing walls 1010 provided behind the cockpit 1002, the partition wall 1012 that partitions between the first class and the economy class, and the partition wall 1014 that partitions the plurality of galleys 26 includes the core 2250 that has a honeycomb structure and is made of a synthetic fibrous material and the surface plate 2252 that is made of a fiber reinforced plastic and attached to both surfaces of the core 2250 as illustrated in FIG. 3.

A reinforcement frame 40 is provided at a location of the first side wall 2206 to which the lower bracket 36A and the upper bracket 38A are attached.

As illustrated in FIGS. 1 and 3, the reinforcement frame 40 includes two thin reinforcement plates 4002 having large contours within which both the base plate portion 3602 of the lower bracket 36A and the mounting plate portion 3802 of the upper bracket 38A can be accommodated.

The thin reinforcement plates 4002 are made of a lightweight material having strength and rigidity higher than those of the surface plate 2252. As such a material, a metal material, a glass fiber reinforced plastic, or the like can be employed.

The thin reinforcement plates 4002 are attached to respective recess portions provided in the core 2250 such that the surfaces of the thin reinforcement plates 4002 and the surfaces of the core 2250 at portions where the thin reinforcement plates 4002 are not provided are positioned on the same planes.

A female thread member 42 having a female thread 4202 that can be engaged with the male thread of the first bolt B1 or the second bolt B2 is embedded in locations of the first side wall 2206 corresponding to the first bolt insertion holes H1 of the base plate portion 3602 and the second bolt insertion holes H2 of the mounting plate portion 3802.

The female thread member 42 is made of an alloy and includes a large diameter portion 4204 and a small diameter portion 4206 on each side. The small diameter portions 4206 on both sides are respectively inserted into holes of the thin reinforcement plates 4002 and the surface plates 2252, and an end surface of the large diameter portion 4204 on each side is disposed in contact with the thin reinforcement plate 4002.

That is, the locations of the first side wall 2206 where the female thread members 42 are disposed are reinforced by the reinforcement frame 40 provided inside the first side wall 2206.

When the pump-type bottle 30 is replenished with the disinfectant, the upper bracket 38A is detached from the first side wall 2206 by removing the second bolts B2 using a tool such as a hexagonal wrench, the pump-type bottle 30 is removed from the lower bracket 38A, the container 3002 is replenished with the disinfectant, and then the upper bracket 38A is attached again to the first side wall 2206 with the second bolts B2.

Alternatively, the lower bracket 36A is detached from the first side wall 2206 by removing the first bolts B1 using a tool such as a hexagonal wrench, the cap 3010 is removed from the container 3002, the container 3002 is replenished with the disinfectant, and then the cap 3010 is attached to the container 3002 and the lower bracket 36A is attached to the first side wall 2206 with the first bolts B1.

That is, the pump-type bottle 30 is configured to be removable from the arrangement instrument 34 by detaching at least one of the lower support member 36 or the upper support member 38 from the wall portion by turning the second bolts B2 or the first bolts B1 with a tool.

According to the first embodiment described above, the pump-type bottle 30 that can discharge a disinfectant for hands and fingers is disposed via the arrangement instrument 34 at the first side wall 2206 of the aircraft lavatory unit 22, which is a wall portion provided in the cabin, at a height at which a passenger can push down the head portion 3016.

Thus, in disposing the pump-type bottle 30 that can discharge a disinfectant for hands and fingers, a wall portion in the cabin is used, thus a placement platform dedicated to the pump-type bottle 30 is unnecessary, and the pump-type bottle 30 can be disposed in the cabin without a space on the floor in the cabin.

In disposing the pump-type bottle 30, a placement platform dedicated to the pump-type bottle 30 is unnecessary, and the arrangement instrument 34 smaller and lighter than the placement platform is used. This is advantageous in reducing the weight of the structure for disposing the pump-type bottle 30 in the cabin and can dispose the pump-type bottle 30 in the cabin while reducing the weight.

Accordingly, the pump-type bottle 30 that can discharge a disinfectant for hands and fingers can be disposed in the aircraft cabin, which is advantageous in preventing the infections with the novel coronavirus in the cabin.

Since the arrangement instrument 34 is includes two members, i.e., the lower support member 36 (lower bracket 36A) and the upper support member 38 (upper bracket 38A) separated from the lower support member 36, the arrangement instrument 34 itself can be reduced in size and weight, and the pump-type bottle 30 can be disposed at the first side wall 2206 while reducing the weight of the arrangement instrument 34.

Further, since the arrangement instrument 34 includes the lower support member 36 (lower bracket 36A) that supports the lower portion of the pump-type bottle 30 while regulating the horizontal movement of the container 3002 and the upper support member 38 (upper bracket 38A) that regulates the upward movement of the pump-type bottle 30 at the upper portion of the pump-type bottle 30, the pump-type bottle 30 can be fixedly supported by the arrangement instrument 34 including the lower bracket 36A and the upper bracket 38A even when the aircraft runs into turbulence and the fuselage 10 violently shakes in the vertical direction and the horizontal direction, which is advantageous in preventing the pump-type bottle 30 from falling out of the arrangement instrument 34.

Furthermore, the pump-type bottle 30 can be removed from the arrangement instrument 34 by detaching at least one of the lower support member 36 or the upper support member 38 from the wall portion by a troublesome operation of turning the second bolts B2 or the first bolts B1 using a tool.

Accordingly, a passenger cannot easily remove the arrangement instrument 34, which is advantageous in preventing the pump-type bottle 30 from being taken out of the arrangement instrument 34 by a passenger.

In addition, the female thread members 42 are disposed inside the first side wall 2206, the first bolts B1 and the second bolts B2 for fixing the lower support member 36 (lower bracket 36A) and the upper support member 38 (upper bracket 38A) are engaged with the female thread members 42, and the location of the first side wall 2206 in which the female thread members 42 are disposed, that is, the first side wall 2206 at which the pump-type bottle 30 is disposed is reinforced by the reinforcement frame 40.

Thus, when a passenger staggers and lays his/her hand on or leans against the pump-type bottle 30 due to the aircraft running into air turbulence and thereby large force is applied to the lower bracket 36A and the upper bracket 38A, the lower bracket 36A and the upper bracket 38A can be fixedly held by the first side wall 2206 via the female thread members 42, which is advantageous in preventing detachment of the lower bracket 36A and the upper bracket 38A including the pump-type bottle 30 from the first side wall 2206.

In addition, the reinforcement frame 40 is provided inside the first side wall 2206, which is advantageous in disposing the pump-type bottle 30 at the aircraft lavatory unit 22 without impairing the appearance of the first side wall 2206 of the aircraft lavatory unit 22.

The lower bracket 36A consisting of the base plate portion 3602, the upper plate portion 3604, and the connecting plate portion 3608 has a substantially triangular frame shape in a side view as illustrated in FIG. 4B, in other words, has a closed cross-sectional shape, the shape itself has strength and rigidity, and the lower bracket 36A is provided with strength and rigidity so as to be unbreakable with force of 136 kg-force (kgf) in the vertical direction or force of 136 kg-force (kgf) in the horizontal direction.

Thus, it is advantageous in preventing the breakage of the lower bracket 36A due to the application of force of 136 kg-force (kgf) in the vertical direction or force of 136 kg-force (kgf) in the horizontal direction when a passenger staggers and lays his/her hand on or leans against the pump-type bottle 30 in the case where the aircraft runs into air turbulence and the fuselage violently shakes in the vertical direction and the horizontal direction.

In addition, with the base plate portion 3602 attached to the first side wall 2206, all of the base plate portion 3602, the upper plate portion 3604, and the connecting plate portion 3608 extend in the horizontal direction, in other words, extend in the same direction. Thus, the lower bracket 36A can be easily manufactured by extrusion molding, which is advantageous in reducing the cost of the lower bracket 36A.

Figure 6:
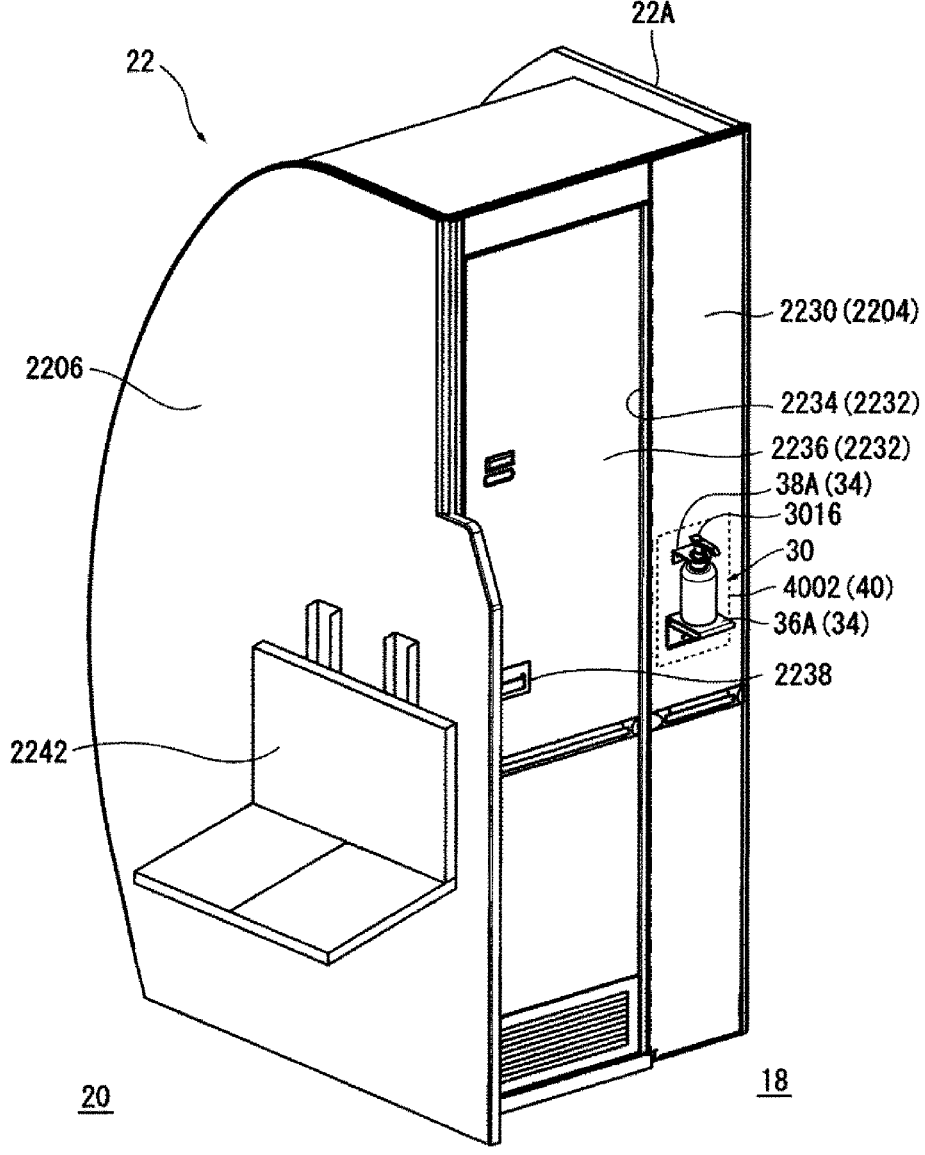
FIG. 6 is a perspective view of an aircraft lavatory unit to which a second embodiment is applied.

Next, a second embodiment will be described with reference to FIG. 6.

In the embodiments described below, the same sections and members as those of the first embodiment will be denoted by the same reference signs, the descriptions thereof will be simplified or omitted, and different sections from the first embodiment will be mainly described.

The second embodiment differs from the first embodiment in a placement position of the pump-type bottle 30.

That is, in the second embodiment, the pump-type bottle 30 is disposed at the front wall body 2230 of the front wall 2204 facing the longitudinal aisle 18 via the arrangement instrument 34 at a height at which a passenger can push down the head portion 3016. Thus, since the pump-type bottle 30 is disposed lateral to the entrance 2232, that is, the pump-type bottle 30 is disposed at a location closer to the entrance 2232 than that in the first embodiment, passengers can more easily disinfect their hands and fingers every time they use the aircraft lavatory unit 22.

As illustrated in FIG. 3, similar to the first side wall 2206, the front wall body 2230 includes the core 2250 that has a honeycomb structure and is made of a synthetic fibrous material and the surface plate 2252 that is made of a fiber reinforced plastic and attached to both surfaces of the core 2250, and the reinforcement frame 40 including the two thin reinforcement plates 4002 is provided at a portion of the front wall body 2230 to which the lower bracket 36A and the upper bracket 38A are attached.

The first bolts B1 and the second bolts B2 respectively inserted into the first bolt insertion holes H1 of the base plate portion 3602 of the lower bracket 36A and the second bolt insertion holes H2 of the mounting plate portion 3802 of the upper bracket 38A are engaged with the female thread members 42 that are embedded in the front wall body 2230 and sandwiched between the thin reinforcement plates 4002.

According to the second embodiment, the pump-type bottle 30 is disposed via the arrangement instrument 34 at the front wall body 2230 at a height at which a passenger can push down the head portion 3016, and thus the same effects as in the first embodiment can be exhibited, which is advantageous in preventing the infections with the novel coronavirus in the aircraft cabin.

Figure 7A:
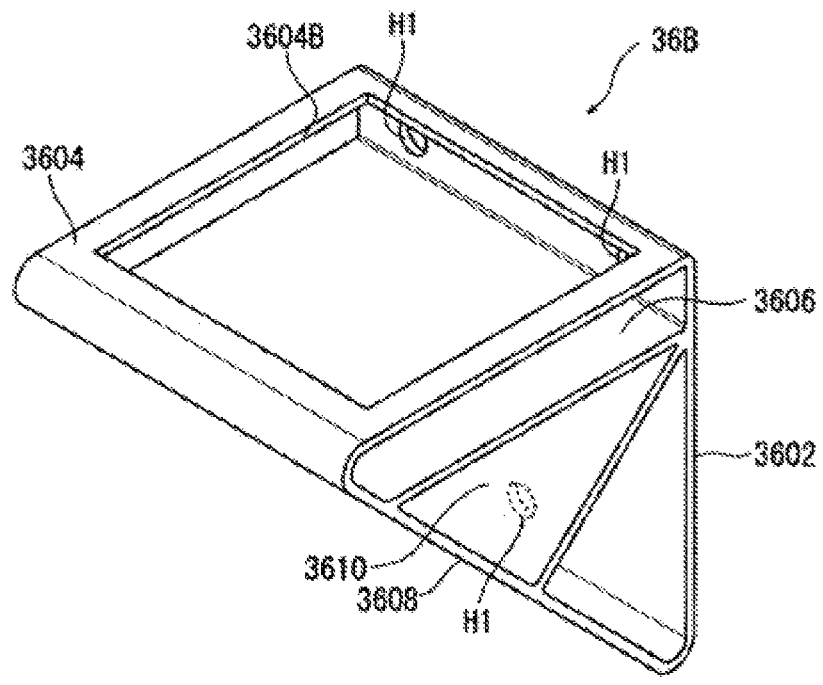
FIG. 7A is a perspective view of a lower bracket according to a third embodiment.

Next, a third embodiment will be described with reference to FIGS. 7A-7B.

The third embodiment has a different configuration from that of the lower bracket 36A of the first and the second embodiments and the other configurations similar to that of the first and the second embodiments.

First, in a lower bracket 36B of the third embodiment, a lower insertion hole 3604B provided in the upper plate portion 3604 is formed in a rectangular shape in the third embodiment, while the lower insertion hole is formed in a circular shape in the first and the second embodiments.

Similar to the first embodiment, the lower portion of the container 3002 of the pump-type bottle 30 is removably inserted into the lower insertion hole 3604B having a rectangular shape, and the lower insertion hole 3604B regulates the horizontal movement of the lower portion of the container 3002 with the lower portion of the container 3002 inserted therein.

The lower bracket 36B includes a reinforcement plate portion 3610 in addition to the base plate portion 3602, the upper plate portion 3604, the placement plate portion 3606, and the connecting plate portion 3608.

The reinforcement plate portion 3610 protrudes obliquely downward from the base plate portion 3602 at a portion from which the placement plate portion 3606 protrudes and is connected to the connecting plate portion 3608.

Figure 7B:
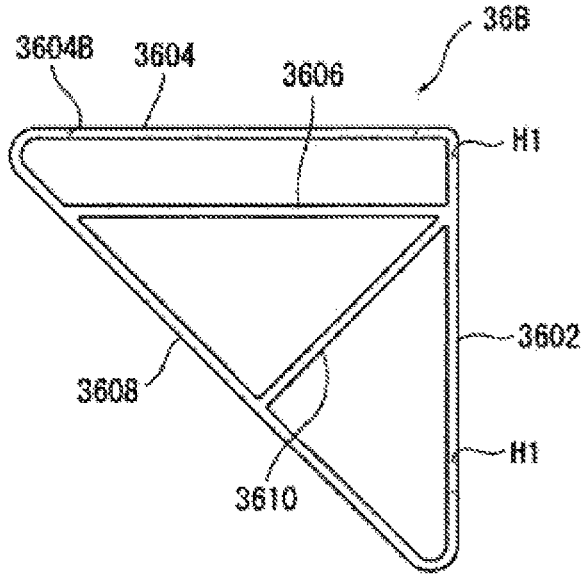
FIG. 7B is a side view thereof.

Similar to the first and the second embodiments, as illustrated in FIG. 7B, the lower bracket 36B has a substantially triangular frame shape in a side view formed by the base plate portion 3602, the upper plate portion 3604, and the connecting plate portion 3608, in other words, has a closed cross-sectional shape, and thus the shape itself has strength and rigidity. In addition, in the third embodiment, since the reinforcement plate portion 3610 is provided, the strength and the rigidity of the lower bracket 36B are further enhanced.

Thus, it is more advantageous in preventing the breakage of the lower bracket 36B due to the application of force of 136 kg-force (kgf) in the vertical direction or force of 136 kg-force (kgf) in the horizontal direction when a passenger staggers and lays his/her hand on or leans against the pump-type bottle 30 in the case where the aircraft runs into air turbulence and the fuselage 10 violently shakes in the vertical direction and the horizontal direction.

In addition, with the base plate portion 3602 attached to the first side wall 2206, all of the base plate portion 3602, the upper plate portion 3604, the connecting plate portion 3608, and the reinforcement plate portion 3610 extend in the horizontal direction, in other words, extend in the same direction. Thus, the lower bracket 36B can be easily manufactured by extrusion molding, which is advantageous in reducing the cost of the lower bracket 36B.

The same effects as in the first and the second embodiments are also exhibited by the third embodiment, which is advantageous in preventing the infections with the novel coronavirus in the aircraft cabin.

Next, a fourth embodiment will be described with reference to FIGS. 8 to 10B.

The fourth embodiment has a different configuration from that of the lower bracket 36A of the first embodiment and the other configurations similar to that of the first embodiment.

Note that, in the following embodiments, cases where the pump-type bottle 30 is disposed at the first side wall 2206 will be described.

Figure 8:
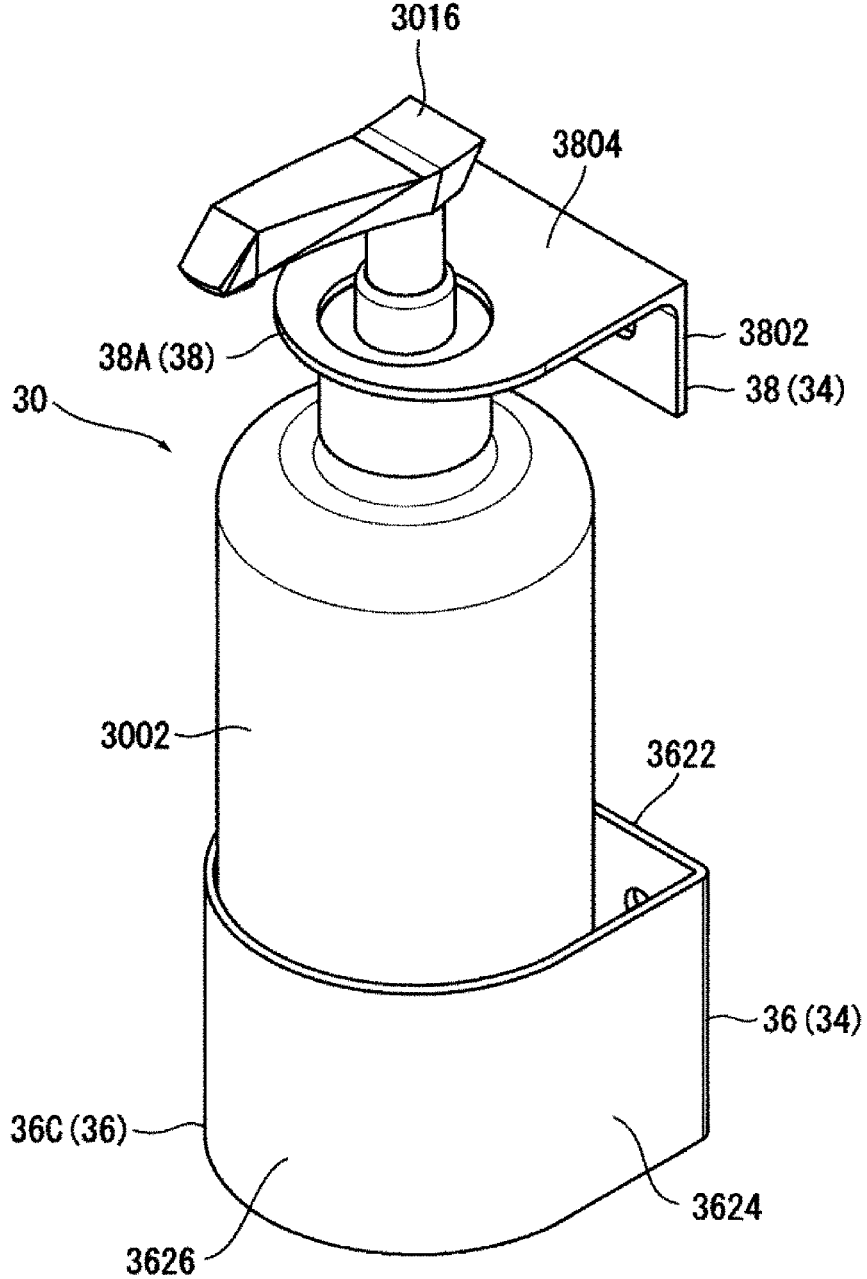
FIG. 8 is a perspective view illustrating the pump-type bottle disposed at the first side wall by using an arrangement instrument according to a fourth embodiment, in which male thread members are omitted to clarify the structure of the arrangement instrument.
Figure 9:
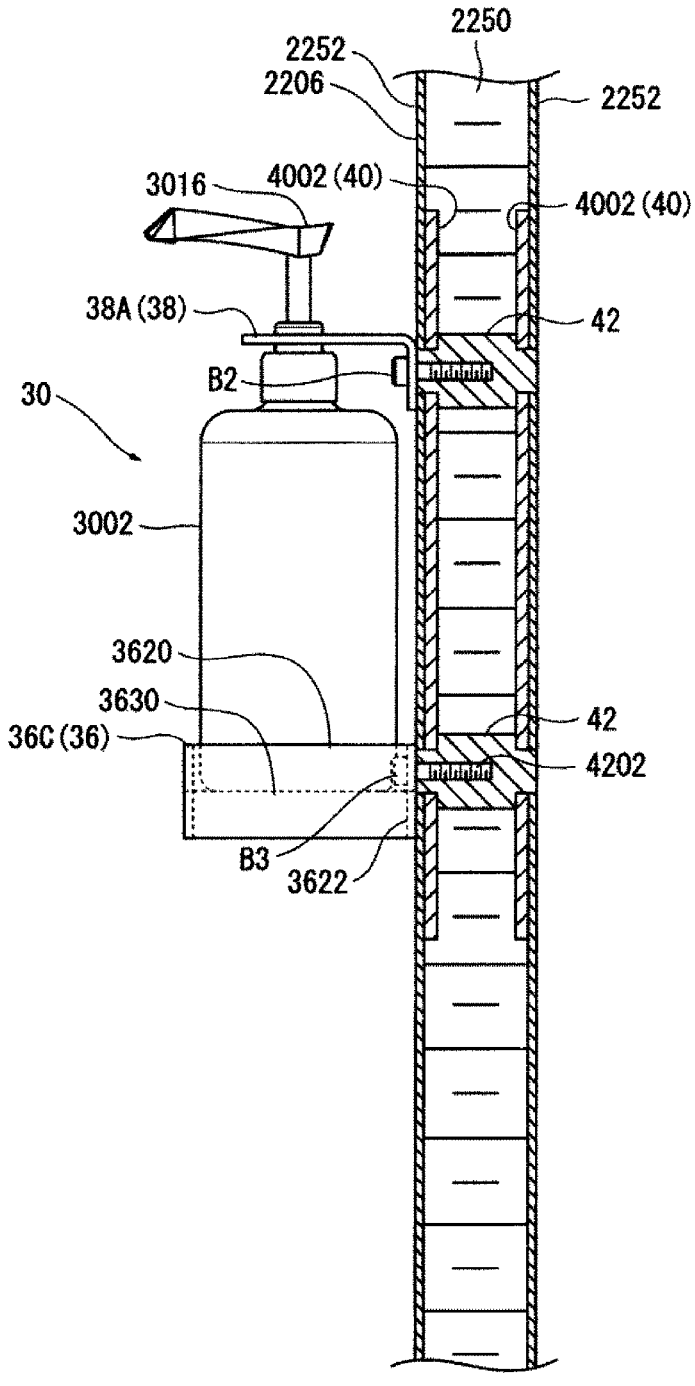
FIG. 9 is a cross-sectional view illustrating the pump-type bottle disposed at the first side wall by using the arrangement instrument according to the fourth embodiment.

As illustrated in FIGS. 8 and 9, a lower bracket 36C of the fourth embodiment is attached to the first side wall 2206. Similar to the first embodiment, the lower bracket 36C is made of an alloy or a fiber reinforced plastic and is preferably made of an aluminum alloy in view of strength, lightness, processability, and design. In the present embodiment, the lower bracket 36C is made of an aluminum alloy.

Figure 10A:
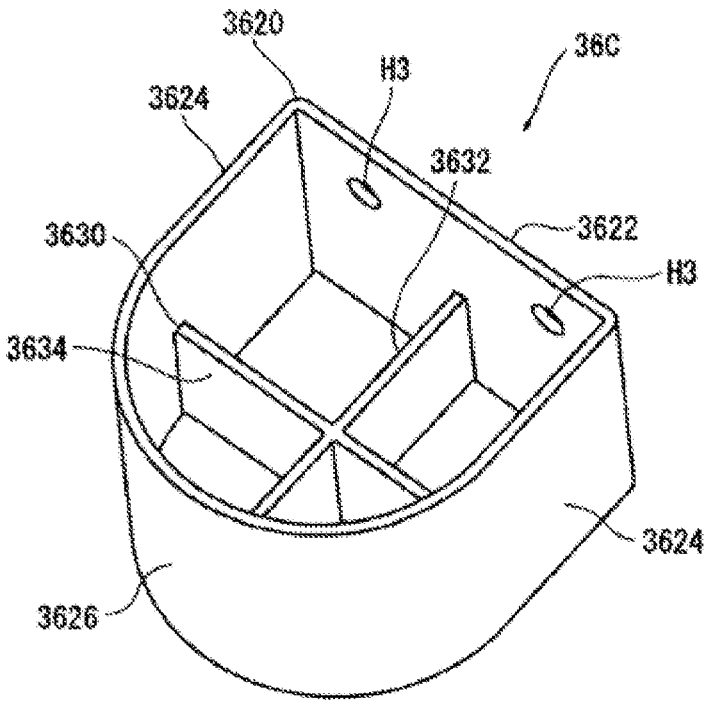
FIG. 10A is a perspective view of a lower bracket according to the fourth embodiment.
Figure 10B:
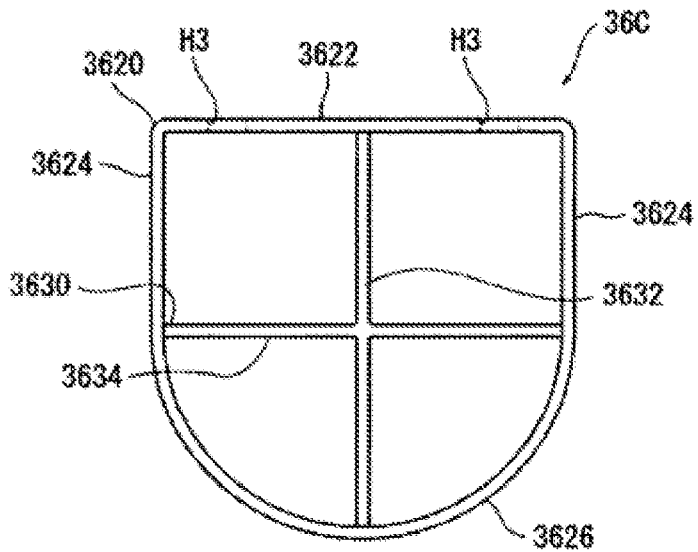
FIG. 10B is a plan view thereof.

As illustrated in FIGS. 10A-10B, the lower bracket 36C includes a peripheral wall 3620 and a bottom wall 3630.

The peripheral wall 3620 is a portion into which the lower portion of the container 3002 of the pump-type bottle 30 is inserted and which regulates the horizontal movement of the pump-type bottle 30.

The peripheral wall 3620 includes a base plate portion 3622 to be placed on the first side wall 2206 and attached to the first side wall 2206 and having an elongated shape, a side plate portion 3624 on each side that protrudes from each side of the base plate portion 3622, and a curved plate portion 3626 that connects ends of the side plate portions 3624 on both sides.

An inner surface of the base plate portion 3622, inner surfaces of the side plate portions 3624 on both sides, and an inner surface of the curved plate portion 3626 are formed in such dimensions that the lower portion of the container 3002 of the pump-type bottle 30 can be inserted and removed and that the horizontal movement of the lower portion of the container 3002 can be regulated.

A third bolt insertion hole H3 is provided on each side of an upper portion of the base plate portion 3622, and as illustrated in FIG. 9, male threads of third bolts B3 (hexagonal socket bolts), which are male thread members inserted into the third bolt insertion holes H3, are engaged with the female threads 4202 of the female thread members 42 embedded in locations of the first side wall 2206 reinforced by the reinforcement frame 40, similar to the first embodiment.

Thus, the lower bracket 36C is removed from the first side wall 2206 by removing the two third bolts B3 from the female thread members 42 of the first side wall 2206.

The bottom wall 3630 is a portion that is provided at the peripheral wall 3620 and supports the lower portion of the pump-type bottle 30.

As illustrated in FIGS. 10A-10B, the bottom wall 3630 is constituted by a plurality of wall portions that connect lower portions of opposed inner surfaces of the peripheral wall 3620 in an inner lower portion of the peripheral wall 3620.

In the present embodiment, the bottom wall 3630 includes a first bottom wall portion 3632 and a second bottom wall portion 3634 that are orthogonal to each other.

The first bottom wall portion 3632 connects a central portion in the extension direction of the curved plate portion 3626 and a central portion in the extension direction of the base plate portion 3622.

The second bottom wall portion 3634 connects the boundary portions between the curved plate portion 3626 and the side plate portions 3624 mutually opposed.

The lower bracket 36C consisting of the peripheral wall 3620 and the bottom wall 3630 has a substantially rectangular frame shape including the curved plate portion 3626 in a plan view, in other words, has a closed cross-sectional shape, includes the bottom wall 3630 that connects mutually-opposed portions of the inner surfaces of the peripheral wall 3620, and thus the shape itself has strength and rigidity.

In addition, with the base plate portion 3622 attached to the first side wall 2206, the peripheral wall 3620 and the bottom wall 3630 extend in the vertical direction, in other words, extend in the same direction. Thus, the lower bracket 36C can be easily manufactured by extrusion molding, which is advantageous in reducing the cost of the lower bracket 36C.

The lower bracket 36C is provided by cutting the first bottom wall portion 3632 and the second bottom wall portion 3634 to heights lower than the height of the peripheral wall 3620 after the extrusion molding.

According to the fourth embodiment described above, the pump-type bottle 30 is disposed via the arrangement instrument 34 at the first side wall 2206 at a height at which a passenger can push down the head portion 3016, and the arrangement instrument 34 includes two separated members, i.e., the lower support member 36 (lower bracket 36C) that supports the lower portion of the pump-type bottle 30 while regulating the horizontal movement of the container 3002 and the upper support member 38 (upper bracket 38A) that regulates the upward movement of the pump-type bottle 30 at the upper portion of the pump-type bottle 30. Thus, the same effects as the first embodiment are exhibited, which is advantageous in preventing the infections with the novel coronavirus in the aircraft cabin.

Figure 11A:
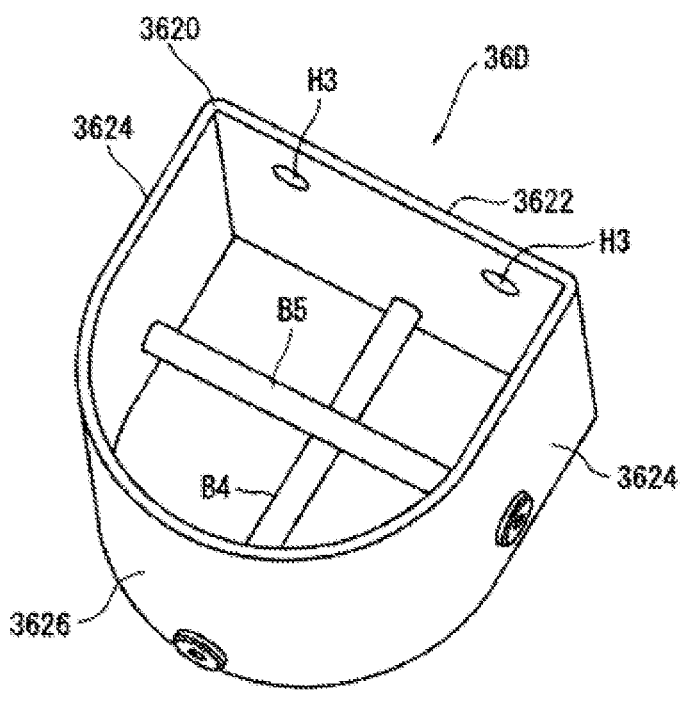
FIG. 11A is a perspective view of a lower bracket according to a fifth embodiment.

Next, a fifth embodiment will be described with reference to FIGS. 11A-11B.

The fifth embodiment is a modified example of the fourth embodiment and differs from the fourth embodiment in the structure of the bottom portion of the lower bracket 36C.

That is, while the bottom portion of the lower bracket 36C of the fourth embodiment includes the first bottom wall portion 3632 and the second bottom wall portion 3634, the bottom portion of a lower bracket 36D of the fifth embodiment includes a plurality of bolts that are male tread members, and thus the bottom portion of the lower bracket 36D is simply formed by the plurality of bolts.

In the present embodiment, the bottom portion of the lower bracket 36D, in other words, the bottom portion of the peripheral wall 3620 includes two bolts, i.e., a fourth bolt B4 (hexagonal socket bolt) and a fifth bolt B5 (hexagonal socket bolt).

Similar to the fourth embodiment, the peripheral wall 3620 includes the base plate portion 3622 having an elongated shape, the side plate portions 3624 on both sides, and the curved plate portion 3626, and the third bolt insertion hole H3 is provided on each side of the upper portion of the base plate portion 3622.

Figure 11B:
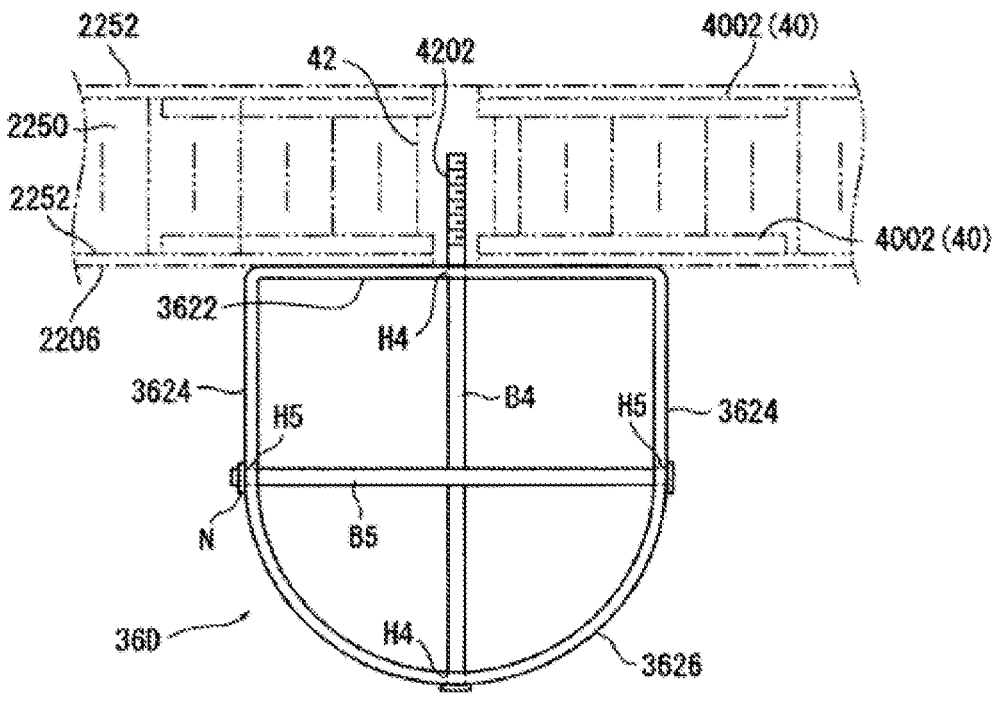
FIG. 11B is a plan view of the lower bracket in which a fourth bolt constituting a bottom portion of the lower bracket is attached to the first side wall.

Further, as illustrated in FIG. 11B, a fourth bolt insertion hole H4 is coaxially provided at each of the center of a lower portion of the base plate portion 3622 and the center of a lower portion of the curved plate portion 3626 facing the center of the lower portion of the base plate portion 3622.

Fifth bolt insertion holes H5 are coaxially provided at portions of the side plate portions 3624 on both sides close to the curved plate portion 3626.

The third bolt B3 is inserted into each of the third bolt insertion holes H3 in the upper portion of the base plate portion 3622, and similar to the fourth embodiment illustrated in FIG. 9, the male threads of the third bolts B3 are engaged with the female threads 4202 of the female thread members 42 embedded in the locations of the first side wall 2206 reinforced by the reinforcement frame 40.

As illustrated in FIG. 11B, the fourth bolt B4 (hexagonal socket bolt), which is one of the plurality of bolts constituting the bottom portion of the lower bracket 36D, extends perpendicularly to the first side wall 2206.

That is, the fourth bolt B4 is inserted from the fourth bolt insertion hole H4 provided in the curved plate portion 3626 to the fourth bolt insertion hole H4 provided in the base plate portion 3622, and a male thread of the fourth bolt B4 is engaged with the female thread 4202 of the female thread member 42 embedded in the location of the first side wall 2206 reinforced by the reinforcement frame 40.

Thus, in the fifth embodiment, since the number of bolts for attaching the lower bracket 36D to the first side wall 2206 is increased by one as compared with the fourth embodiment, the attachment strength of the lower bracket 36D is increased as compared with the fourth embodiment.

The fifth bolt B5 is inserted from one of the fifth bolt insertion holes H5 to the other one of the fifth bolt insertion holes H5, and a nut N is engaged with a male thread of the fifth bolt B5 protruding to the outside of the side plate portion 3624, thereby the fifth bolt B5 is attached to the side plate portion 3624 on both sides.

The fourth bolt B4 and the fifth bolt B5 are orthogonal to each other in a plan view, and the fifth bolt B5 is located above the fourth bolt B4.

With the base plate portion 3622 attached to the first side wall 2206, the base plate portion 3622, the side plate portions 3624 on both sides, and the curved plate portion 3626 extend in the vertical direction, and thus the peripheral wall 3620 can be easily manufactured by extrusion molding similar to the fourth embodiment, which is advantageous in reducing cost.

The lower bracket 36D is removed from the first side wall 2206 by removing the fourth bolt B4 in addition to the two third bolts B3 from the female thread members 42 of the first side wall 2206 by using a tool.

According to the fifth embodiment, similar to the fourth embodiment, the horizontal movement of the lower portion of the container 3002 is regulated by the peripheral wall 3620 of the lower bracket 36D, the bottom portion of the container 3002 is supported by the fourth bolt B4 and the fifth bolt B5, and the upward movement of the pump-type bottle 30 is regulated by the upper bracket 38A. Thus, the same effects as the first embodiment are exhibited, which is advantageous in preventing the infections with the novel coronavirus in the aircraft cabin.

Figure 12:
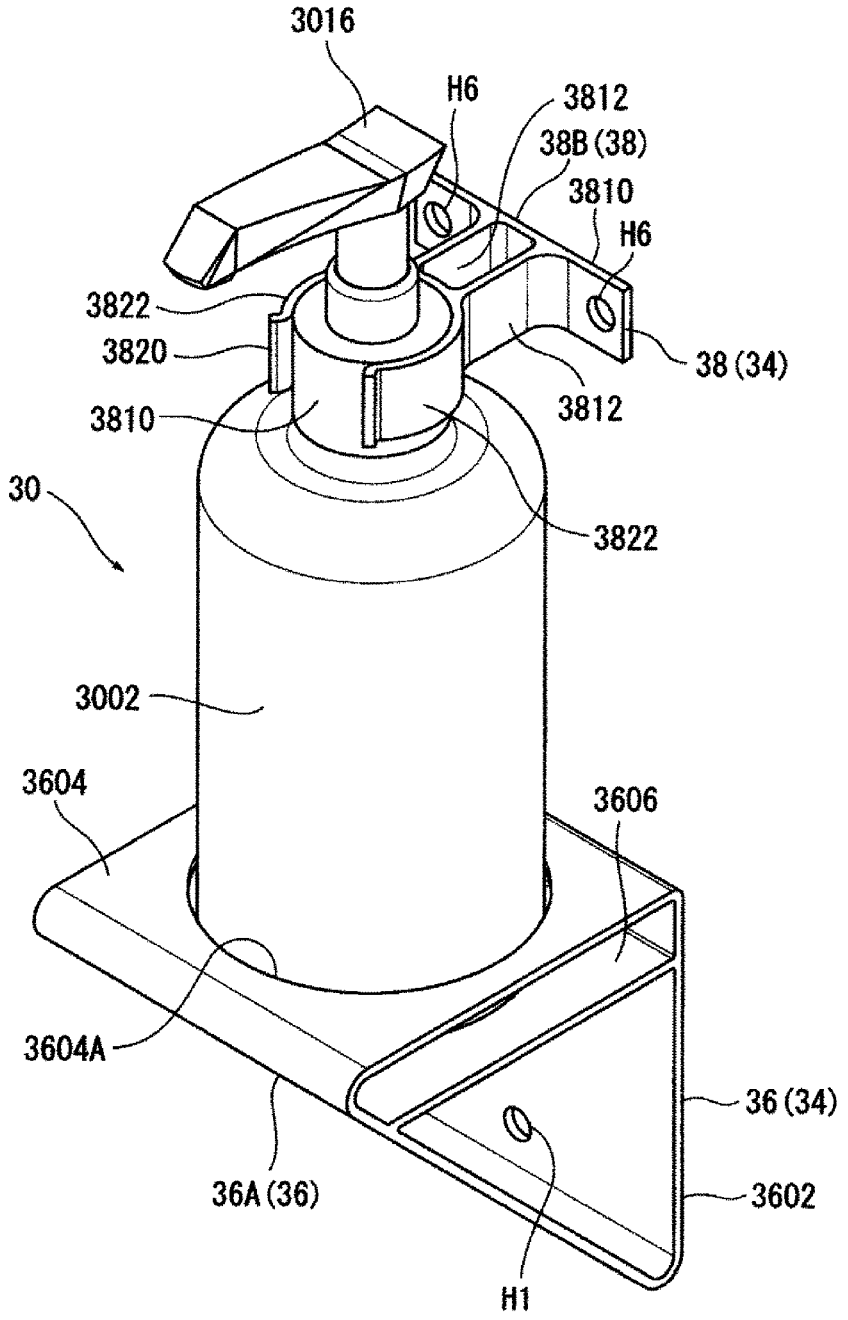
FIG. 12 is a perspective view illustrating the pump-type bottle disposed at the first side wall by using an arrangement instrument according to a sixth embodiment, in which male thread members are omitted to clarify the structure of the arrangement instrument.

Next, a sixth embodiment will be described with reference to FIGS. 12 and 13.

The sixth embodiment has a different configuration from that of the upper bracket 38A of the first embodiment and the other configurations similar to that of the first embodiment.

Similar to the first embodiment, an upper bracket 38B of the sixth embodiment is made of an alloy or a fiber reinforced plastic and is preferably made of an aluminum alloy in view of strength, lightness, processability, and design. In the present embodiment, the upper bracket 38B is made of an aluminum alloy.

The upper bracket 38B includes a mounting plate portion 3810 and a clamping portion 3820, and has a simpler configuration, a smaller size, and a lighter weight than the lower support member 36 and is advantageous in reducing the weight and cost of the upper support member 38, that is, reducing the weight and cost of the arrangement instrument 34.

The mounting plate portion 3810 has an elongated rectangular shape and includes two sixth bolt insertion holes H6 in the mounting plate portion 3810.

Figure 13:
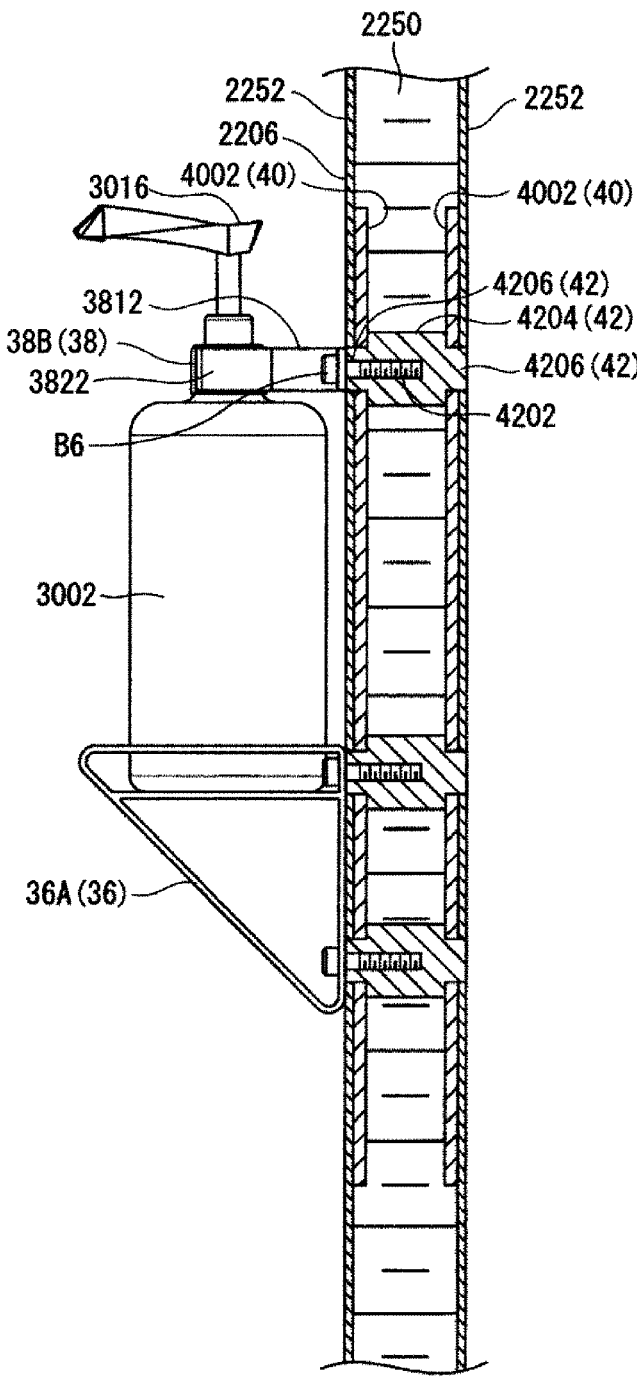
FIG. 13 is a cross-sectional view illustrating the pump-type bottle disposed at the first side wall by using the arrangement instrument according to the sixth embodiment.

As illustrated in FIG. 13, the mounting plate portion 3810 is placed on a location of the first side wall 2206 separated upward from the lower bracket 36A and is attached to the first side wall 2206 by using sixth bolts B6 (hexagonal socket bolts) which are male thread members inserted into the sixth bolt insertion holes H6.

Similar to the first embodiment, the male threads of the sixth bolts B6 are engaged with the female threads 4202 of the female thread members 42 embedded in the locations of the first side wall 2206 reinforced by the reinforcement frame 40.

A pair of arm portions 3812 are disposed protruding from the center in the length direction of the mounting plate portion 3810, and the clamping portions 3820 are provided at tip portions of the arm portions 3812.

The clamping portion 3820 includes two clamping pieces 3822 having an arcuate shape facing each other.

In the present embodiment, base portions of the two clamping pieces 3822 are connected.

The two clamping pieces 3822 are configured to be able to clamp the cap 3010 at the upper portion of the pump-type bottle 30.

Thus, by pushing the cap 3010 into between the two clamping pieces 3822, the cap 3010 is clamped by the two clamping pieces 3822, and the horizontal movement and the upward movement of the cap 3010 are regulated by the two clamping pieces 3822.

For example, when the pump-type bottle 30 is replenished with the disinfectant, the upper bracket 38B is removed from the first side wall 2206 by removing the two sixth bolts B6 from the female thread members 42 of the first side wall 2206 by using a tool.

Accordingly, the lower portion of the pump-type bottle 30 is supported from below and the horizontal movement thereof is regulated by the lower bracket 36A, and the upward movement of the pump-type bottle 30 is regulated by the upper bracket 38B. Thus, also in the sixth embodiment, the same effects as the first embodiment are exhibited, which is advantageous in preventing the infections with the novel coronavirus in the aircraft cabin.

Figure 14:
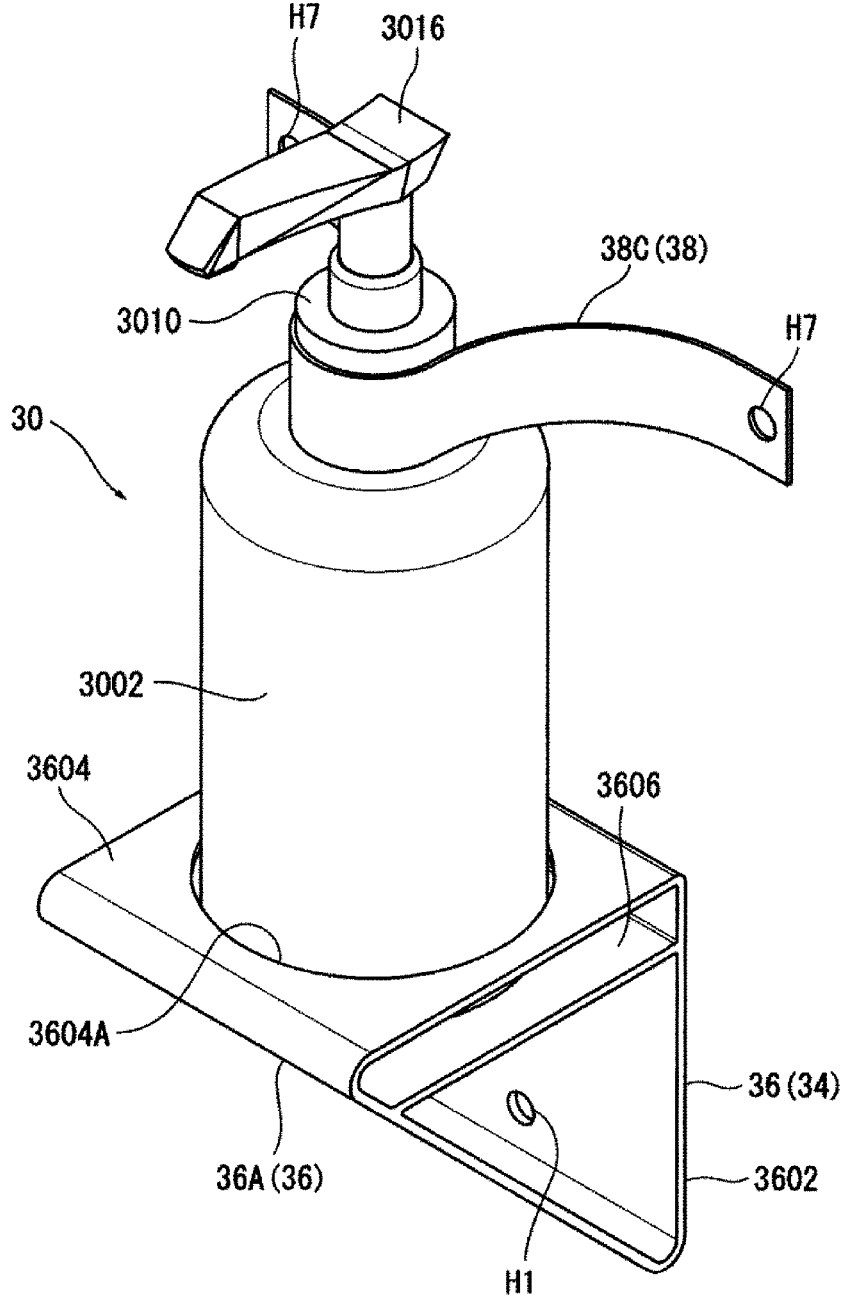
FIG. 14 is a perspective view illustrating the pump-type bottle disposed at the first side wall by using an arrangement instrument according to a seventh embodiment, in which male thread members are omitted to clarify the structure of the arrangement instrument.

Next, a seventh embodiment will be described with reference to FIGS. 14 and 15.

The seventh embodiment has a different configuration of the upper support member 38 of the arrangement instrument 34 from that of the first embodiment in the configuration and the other configurations similar to that of the first embodiment.

In the seventh embodiment, the upper support member 38 includes a band 38C having an elongated shape that is made of an elastic material and has flexibility. The upper support member 38 has a simpler configuration, a smaller size, and a lighter weight than the lower support member 36 and is advantageous in reducing the weight and cost thereof, that is, reducing the weight and cost of the arrangement instrument 34.

The band 38C is embedded with a mesh or cord made of a metal so that the band 38C is not easily cut and that a passenger cannot easily take the pump-type bottle 30 out of the arrangement instrument 34.

Figure 15:
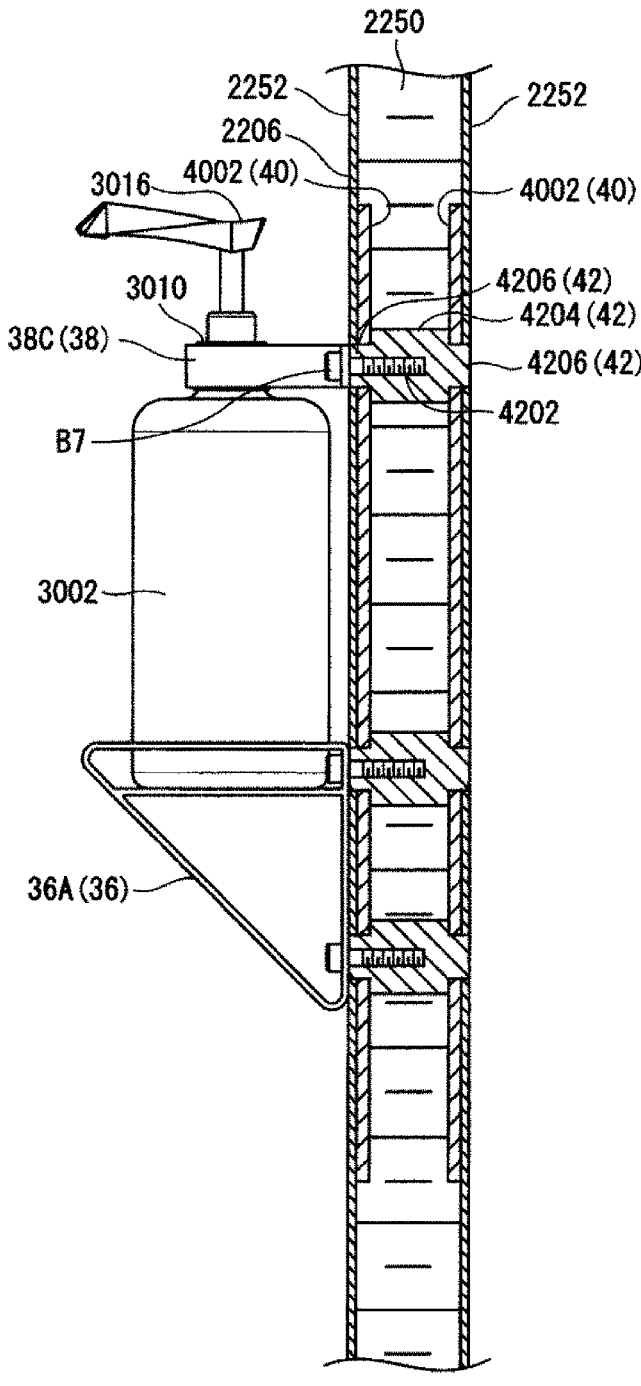
FIG. 15 is a cross-sectional view illustrating the pump-type bottle disposed at the first side wall by using the arrangement instrument according to the seventh embodiment.

Seventh bolt insertion holes H7 are provided at both ends in the longitudinal direction of the band 38C, and the band 38C is attached to a location of the first side wall 2206 separated upward from the lower bracket 36A by using seventh bolts B7 (hexagonal socket bolts) which are male thread members inserted into the seventh bolt insertion holes H7 as illustrated in FIG. 15.

Similar to the first embodiment, the male threads of the seventh bolts B7 are engaged with the female threads 4202 of the female thread members 42 embedded in the locations of the first side wall 2206 reinforced by the reinforcement frame 40.

An intermediate portion of the band 38C in the longitudinal direction comes in elastic contact with the cap 3010 at the upper portion of the pump-type bottle 30 to bias the cap 3010 toward the first side wall 2206 and regulates the horizontal movement and the upward movement of the upper portion of the pump-type bottle 30.

Accordingly, the lower portion of the pump-type bottle 30 is supported from below and the horizontal movement thereof is regulated by the lower bracket 36A, and the upward movement of the pump-type bottle 30 is regulated by the band 38C.

In the case of replenishment of a disinfectant or the like, the pump-type bottle 30 is removed from the arrangement instrument 34 by removing the seventh bolt B7 located at one end of the band 38C in the longitudinal direction from the first side wall 2206. This requires a troublesome operation of turning the seventh bolt B7 by using a tool such as a hexagonal wrench, which is advantageous in preventing the pump-type bottle 30 from being taken out from the arrangement instrument 34 by a passenger.

Accordingly, the lower portion of the pump-type bottle 30 is supported from below the horizontal movement thereof is regulated by the lower bracket 36A, and the upward movement of the pump-type bottle 30 is regulated by the band 38C. Thus, also in the seventh embodiment, the same effects as the first embodiment are exhibited, which is advantageous in preventing the infections with the novel coronavirus in the aircraft cabin.

The configurations of the upper support member 38 of the sixth and the seventh embodiments can also be applied to the first to the fifth embodiments as a matter of course.

The first to the seventh embodiments have described cases in which the pump-type bottle 30 that can discharge a disinfectant for hands and fingers is disposed at a wall portion constituting the structural frame 22A of each of the two aircraft lavatory units 22. However, as illustrated in FIG. 16, a pump-type bottle 30A may be disposed at the plurality of dividing walls 1010 facing the latitudinal aisle 20 behind the cockpit 1002 via the arrangement instrument 34, a pump-type bottle 30B may be disposed at the partition wall 1012 that partitions between the first class and the economy class via the arrangement instrument 34, and a pump-type bottle 30C may be disposed at the partition wall 1014 of the plurality of galleys 26 via the arrangement instrument 34. As a matter of course, the present technology is applied to wall portions provided in the aircraft cabin other than the wall portions of the aircraft lavatory units 22. The larger the number of locations at which the pump-type bottle 30 is disposed in the aircraft cabin is, the more easily disinfection of hands and fingers can be performed, which is advantageous in preventing the infections with the novel coronavirus in the cabin.

The invention claimed is:

1. An arrangement structure for a pump-type bottle in an aircraft cabin in which the pump-type bottle that can discharge a disinfectant for hands and fingers is disposed in the aircraft cabin, comprising an arrangement instrument configured to attach the pump-type bottle being provided on a wall portion of the aircraft cabin, the pump-type bottle being disposed at the wall portion by using the arrangement instrument at a height at which a passenger can push down a head portion of the pump-type bottle, wherein the arrangement instrument comprises two members separated from each other, a lower support member configured to support a lower portion of the pump-type bottle and an upper support member configured to support an upper portion of the pump-type bottle, the lower support member supports the lower portion of the pump-type bottle while regulating a horizontal movement of the pump-type bottle at the lower portion of the pump-type bottle, the upper support member regulates an upward movement of the pump-type bottle at the upper portion of the pump-type bottle, the lower support member comprises a lower bracket to be attached to the wall portion, the lower bracket comprises:

a base plate portion to be placed on the wall portion and attached to the wall portion by using a male thread member, an upper plate portion protruding from an upper end of the base plate portion and comprising a lower insertion hole through which the lower portion of the pump-type bottle is removably inserted, the lower insertion hole being configured to regulate the horizontal movement of the lower portion of the pump-type bottle, a placement plate portion that is disposed protruding from a portion of the base plate portion located below the upper plate portion and on which a bottom portion of the pump-type bottle inserted through the lower insertion hole is placed, and a connecting plate portion protruding obliquely upward from a lower end of the base plate portion and connecting ends of the upper plate portion and the placement plate portion, the base plate portion, the upper plate portion, and the connecting plate portion being formed of a substantially triangular frame shape in a side view and have a closed cross-sectional structure.

2. The arrangement structure for a pump-type bottle in an aircraft cabin according to claim 1, wherein the lower support member and the upper support member are each attached to the wall portion by using a male thread member, and detaching at least one of the lower support member or the upper support member from the wall portion allows for removal of the pump-type bottle from the arrangement instrument.

3. The arrangement structure for a pump-type bottle in an aircraft cabin according to claim 2, wherein the wall portion comprises:

a core made of a synthetic fibrous material and having a honeycomb structure; and a surface plate attached on both sides of the core and made of a fiber reinforced plastic, the male thread member is engaged with a female thread member embedded in the wall portion, and a location of the wall portion in which the female thread member is disposed is reinforced by a reinforcement frame provided inside the wall portion.

4. The arrangement structure for a pump-type bottle in an aircraft cabin according to claim 1, wherein with the base plate portion attached to the wall portion, all of the base plate portion, the upper plate portion, and the connecting plate portion extend in a horizontal direction.

5. The arrangement structure for a pump-type bottle in an aircraft cabin according to claim 1, wherein with the base plate portion attached to the wall portion, the lower bracket comprises a reinforcement plate portion that protrudes obliquely downward in a direction away from the wall portion from a portion of the base plate portion from which the placement plate portion protrudes and is connected to the connecting plate portion.

6. The arrangement structure for a pump-type bottle in an aircraft cabin according to claim 5, wherein with the base plate portion attached to the wall portion, the reinforcement plate portion extends in a horizontal direction together with the base plate portion, the upper plate portion, and the connecting plate portion.

7. The arrangement structure for a pump-type bottle in an aircraft cabin according to claim 1, wherein the lower support member comprises a lower bracket to be attached to the wall portion, the lower bracket comprises:

a peripheral wall into which the lower portion of the pump-type bottle is inserted, the peripheral wall being configured to regulate a horizontal movement of the pump-type bottle; and a bottom wall provided in the peripheral wall and configured to support the lower portion of the pump-type bottle, the peripheral wall comprises a base plate portion to be placed on the wall portion and attached to the wall portion by using a male thread member, the peripheral wall is formed of a substantially rectangular frame shape in a plan view and has a closed cross-sectional structure, and the bottom wall comprises a plurality of wall portions connecting opposed inner surfaces of the peripheral wall in an inner lower portion of the peripheral wall.

8. The arrangement structure for a pump-type bottle in an aircraft cabin according to claim 7, wherein with the base plate portion attached to the wall portion, the peripheral wall and the bottom wall extend in a vertical direction.

9. The arrangement structure for a pump-type bottle in an aircraft cabin according to claim 1, wherein the upper support member comprises an upper bracket to be attached to the wall portion, the upper bracket comprises:

a mounting plate portion to be attached to a location of the wall portion upwardly separated from a lower bracket by using a male thread member; and a protruding plate portion protruding from the mounting plate portion, and the protruding plate portion comprises an insertion hole through which the lower portion of the pump-type bottle is removably inserted, the insertion hole being configured to regulate the upward movement of the pump-type bottle.

10. The arrangement structure for a pump-type bottle in an aircraft cabin according to claim 1, wherein the upper support member comprises a band made of an elastic material and having an elongated shape, both ends of the band in a longitudinal direction are attached to locations of the wall portion upwardly separated from a lower bracket by using the male thread members, and an intermediate portion of the band in the longitudinal direction comes in elastic contact with the upper portion of the pump-type bottle to bias the upper portion of the pump-type bottle toward the wall portion and regulates the upward movement of the pump-type bottle.

* * * * *